United States Patent [19]
Appel

[11] Patent Number: 4,699,875
[45] Date of Patent: Oct. 13, 1987

[54] DIAGNOSIS OF AMYOTROPHIC LATERAL SCLEROSIS BY NEUROTROPHIC FACTORS

[75] Inventor: Stanley H. Appel, Houston, Tex.

[73] Assignee: Baylor College of Medicine, Houston, Tex.

[21] Appl. No.: 769,203

[22] Filed: Aug. 23, 1985

Related U.S. Application Data

[62] Division of Ser. No. 444,293, Nov. 24, 1982, abandoned.

[51] Int. Cl.[4] ................................................ C12D 1/00
[52] U.S. Cl. ......................................................... 435/4
[58] Field of Search ............................................. 435/4

[56] References Cited

U.S. PATENT DOCUMENTS 3,989,819  11/1976  Brockman ............................ 424/95

Primary Examiner—Sam Rosen
Attorney, Agent, or Firm—Ciotti & Murashige, Irell & Manella

[57] ABSTRACT

The present invention is based on the discovery that amyotrophic lateral sclerosis (ALS), Parkinson disease and Alzheimer disease are due to lack of a disorder-specific neurotrophic hormone. Diagnosis is accomplished by assaying hormones specific for a particular neuronal network or system: the motor neurotrophic hormones from muscle in the motor neural system are used to diagnose and treat ALS, dopamine neurotrophic hormones from striatum in the migrostriatal neural system are used to diagnose and treat parkinsonism, and cholinergic neurotrophic hormones released from the cortex and hippocampus which are specific for cholinergic neorons of the nucleus basalis and septal nucleus are used to diagnose and treat Alzheimer's disease. With tissue culture, the presence or absence of specific neurotrophic hormones can be assessed in ALS, parkinsonism, and Alzheimer disease. If there is a deficiency, extracted and purified neurotrophic hormones specific to the particular neuronal network or system can be injected in ALS and Alzheimer disease and in parkinsonism.

3 Claims, No Drawings

DIAGNOSIS OF AMYOTROPHIC LATERAL SCLEROSIS BY NEUROTROPHIC FACTORS

CROSS REFERENCE TO RELATED APPLICATIONS

The present application is a divisional of application Ser. No. 444,293, filed on Nov. 24, 1982, now abandoned.

FIELD OF THE INVENTION

The field of the invention is the diagnosis and treatment of ALS, Parkinson disease, and Alzheimer disease by neurotrophic factors.

BACKGROUND OF THE INVENTION

The causes of some of the most common and most devastating diseases of the nervous system remain unknown. Prominent on this list are amyotrophic lateral sclerosis (ALS), parkinsonism, and Alzheimer disease. Each of these conditions is presently considered to be degenerative disorder of unknown origin. In each, viral or immunological causes have been suggested, but no convincing reproducible data support the presence of an infectious agent or a cell-mediated or humoral immune factor. All three diseases reflect pathological change in a relatively limited network within the peripheral or central nervous system, or both.

Amyotrophic Lateral Sclerosis

Amyotrophic lateral sclerosis is the name given to a complex of disorders that compromise upper and lower motor neurons. Patients may present with progressive spinal muscular atrophy, progressive bulbar palsy, primary lateral sclerosis, or a combination of these conditions. The majority of patients have components of all three types, but each form may represent the sole clinical manifestation of motor system involvement [1]. (Reference numbers are to references listed in the section entitled "References Cited"). At the present time in the United States, the incidence of the combined disease is approximately 1.8 per 100,000 [2] and its prevalence is between 5 and 7 per 100,000. Males are affected more commonly than females, the ratio of males to females being 1.6:1. Approximately 10% of the cases are familial [3]. Onset may occur at any age but is most common in the later decades, and the incidence appears to increase with age. The mean age of onset is 66 years [2].

Distal weakness and atrophy are the hallmarks of the disorder, and both upper and lower motor neurons are affected. Sensory signs are usually absent, although quantitative sensory assessment by electromyography may indicate abnormalities [4]. The extraocular muscles and bladder are rarely involved. Progression usually occurs over 12 to 30 months, and death ensues as a result of severe impairment of breathing functions.

The major pathological abnormality is loss of large motor neurons of the motor cortex, brain-stem, and spinal cord. In remaining motor neurons there is chromatolysis and inclusions that are rich in ribonucleic acid or are Lewy body-like or eosinophilic (Bunina bodies) [5]. The whole neuron seems to be involved, and there is only minimal evidence of "dying back" of the peripheral axons [6]. In addition, large proximal axonal swellings (spheroids) have been reported in motor neurons from patients with ALS [7], and similar abnormalities can be induced in animals following injection of B-B'-iminodipropionitrile, with resulting impairment of slow axonal transport [8]. These spheroids represent abnormalities of neurofilaments and may be found in the cytoplasm as well as in the axon.

Involvement of the motor system has been described in familial conditions appearing at earlier ages [3]. For example, Werdnig-Hoffmann disease presents in utero or in infancy as a rapidly progressive autosomal recessive condition characterized by severe weakness. Kugelberg-Welander disease is first seen in the juvenile period with weakness in the hips and subsequent involvement of the shoulder muscles. It is also inherited as an autosomal recessive disorder, although autosomal dominant and X-linked recessive transmission have been described. Both of these clinical conditions result from anterior horn cell abnormalities and share clinical features with the progressive muscular atrophies appearing later in life.

Parkinsonism

The presence of tremor, bradykinesia, and rigidity and loss of postural reflexes are characteristics of idiopathic parkinsonism. At the present time in the United States, the incidence of this disorder is estimated to be approximately 20 per 100,000 and its prevalence is 200 per 100,000 [9]. There is a slight male to female preponderance with the ratio of males to females being 1.2:1. The mean age of onset appears to be greater than 67 years and, as in ALS, the incidence may increase with age. As in ALS, some 5 to 10% of patients have a family history of the disorder.

The primary pathological abnormality appears to be loss of neurons in the substantia nigra. In addition, eosinophilic cytoplasmic inclusions termed Lewy bodies are present in nigral neurons. In cases of post-encephalitic parkinsonism, neurofibrillary alterations are noted in nigral neurons. The loss of these nigral cells leads to marked impairment in the nigrostriatal pathway and a great diminution in the dopaminergic synaptic input to the caudate and putamen. The enzymes of this incoming pathway that synthesize dopamine are impaired [10]. Of importance is the fact that no diminution is noted in the dopamine receptors within the striatum. In fact, enhancement of receptor sensitivity may well be present [11].

A number of pathological factors may impair nigrostriatal function and thus give rise to secondary parkinsonism. These include infections and postinfectious states; toxins such as manganese, carbon monoxide, or carbon disulfide; drugs including neuroleptic compounds such as phenothiazines, reserpine, and haloperidol; structural lesions such as brain tumors, trauma, or syrinx or vascular disease; as well as metabolic abnormalities such as hypoparathyroidism and basal ganglia calcification.

Alzheimer Disease

Alzheimer disease is a disorder of the later decades of life characterized by dementia. In clinical terms, it consists of a diffuse deterioration of mental function, primarily in thought and memory and secondarily in feeling and conduct. Alzheimer disease has been used to designate dementia appearing before the age of 65 years. When the syndrome presents after that age, the term senile dementia of the Alzheimer type is used. In fact, it appears reasonable to consider both types as representing a single syndrome. The true incidence of the disorder is unknown, although recent data suggest that the incidence of all dementia in the U.S. population may be over 100 cases per 100,000, with its prevalence being over 550 per 100,000 [12]. Alzheimer disease probably affects at least 30 to 50% of patients with dementia, and in the United States there may be over one million individuals with severe dementia and several million more with mild to moderate dementia. It has been estimated that 1 out of every 6 persons over the age of 65 in the United States suffers from moderate dementia, and a majority of patients in nursing home populations are affected with the disorder. The average age of onset is between 70 and 79 years, but without better information on the population at risk, a more accurate statement is not presently possible [12]. As in ALS and parkinsonism, the incidence of the syndrome clearly increases with advancing age. A family history of Alzheimer disease is present in 5 to 10% of the patients.

At the present time, the clinical diagnosis of Alzheimer disease is one of exclusion. Secondary causes of loss of memory and impaired cognitive function may result from multiple infarcts, leading to so-called multiinfarct dementia, or from intracranial mass lesions such as subdural hematomas, brain tumors, or granulomas. Central nervous system infections of viral and bacterial origin, or even slow viral disorders such as Jakob-Creutzfeldt disease, are part of the differential diagnosis. Furthermore, metabolic disorders involving vitamin $B_{12}$ metabolism, thiamine or folate deficiency, thyroid dysfunction, hepatic and renal failure, as well as drug toxicity may present as dementia. Nevertheless, when all these secondary causes, many of which are reversible, are eliminated, cerebral atrophy of unknown cause or Alzheimer disease still covers the largest number of patients. Elevations of aluminum content in brain have been implicated in the pathogenesis of the disorder but appear to be secondary rather than primary [13, 14].

The pathological picture of Alzheimer disease has been well characterized over the years. It consists of senile plaques, which result from degeneration of nerve endings, and neurofibrillary tangles, which represent an alteration in the cytoskeletal apparatus [15]. In addition, intracellular cytoplasmic eosinophilic inclusions, termed Hirano bodies, are present, primarily in the hippocampus. Granulovacuolar degeneration is also noted. Senile plaques and neurofibrillary tangles in the brain are part of the "normal" aging process. However, at any age, patients with clinical Alzheimer disease appear to have a much higher concentration of these abnormalities than do normal individuals [16].

The most recent prominent discovery in Alzheimer disease is a deficiency of the enzyme that synthesizes the neurotransmitter acetylcholine, namely, choline acetyltransferase (CAT) [17]. This deficiency is most marked in the cortex and hippocampus. Of note is the fact that acetylcholine receptors in the brain are either unaffected or relatively less affected. Thus, the defect in CAT reflects an alteration in the presynaptic cholinergic neuron. The diminution in CAT correlates with the presence of senile plaques: the greater the number of plaques, the lower the activity of CAT. Enzymes synthesizing several other neurotransmitters including dopamine, norepinephrine, serotonin, and y-aminobutyric acid, as well as levels of vasoactive intestinal peptide, are all relatively unaffected compared to the loss of CAT activity. Somatostatin-like activity has recently been reported to be decreased in cerebral cortex [18].

The CAT activity found in hippocampus appears to derive largely from nerve terminals for which the cell of origin is in the septal nucleus. In addition, almost 70% of CAT activity in the cortex appears to reside in terminals with cell bodies located in the nucleus basalis of Meynert [19]. In rats, these cholinergic neurons lie intermingled with and beneath the medial globus pallidus, whereas in primates, comparable cells are found exclusively outside the pallidum. In humans, the nucleus basalis of Meynert is situated in the fibrous zone beneath the globus pallidus and is a major component of the substantia innominata [20]. Thus, the cholinergic input to hippocampus and cortex may derive from a group of cells extending from the septal nuclei to constituents of the substantia innominata and may well be impaired in Alzheimer disease [20].

REFERENCES CITED

1. Munsat TL, Bradley WG: Amyotrophic lateral sclerosis. In Tyler HR, Dawson DM (eds): Current Neurology, vol 2. Boston, Houghton Mifflin, 1979
2. Juergens SM, Kurland LT, Okazaki H, Mulder DW: ALS in Rochester, Minn., 1925–1977. Neurology (NY) 30:463–470, 1980
3. Engel WK: Motor neuron disorders. In Goldensohn ES, Appel SH (eds): Scientific Approaches to Clinical Neurology. Philadelphia, Lea & Febiger, 1977, pp 1322–1346
4. Dyck PJ, Stevens JC, Mulder DW, et al: Frequency of nerve fiber degeneration of peripheral motor and sensory neurons in amyotrophic lateral sclerosis: morphometry of deep and superficial peroneal nerve. Neurology (Minneap) 25:781–785, 1975
5. Chou SM: Pathognomy of intraneuronal inclusion in ALS. In Tsubaki T, Toyokura Y (eds): Amyotrophic Lateral Sclerosis. Tokyo, University of Tokyo Press, 1979, pp 135–176
6. Bradley WG, Kelemen J. Adelman LS, et al: The absence of dying-back in the phrenic nerve in amyotrophic lateral sclerosis (ALS). Neurology (NY) 30:409, 1980
7. Carpenter S: Proximal axonal enlargement in motor neuron disease. Neurology (Minneap) 18:841–851, 1968
8. Griffin JW, Hoffman PN, Clark AW, Carroll PT, Price DL: Slow axonal transport of neurofilament proteins: impairment of beta, beta-iminodipropionitrile administration. Science 202:633–635, 1978
9. Marttila RJ, Rinne UK: Changing epidemiology of Parkinson's disease: predicted effects of levodopa treatment. Acta Neurol Scand 59:80–87, 1979
10. Calne DB, Kebabian J, Silbergeld E, et al: Advances in the neuropharmacology of parkinsonism. Ann Intern Med 90:219–229, 1979
11. Burke RE, Fahn S: Movement Disorders. In Appel SH (ed): Current Neurology. New York, Wiley, 1981, vol 3, pp 92–137
12. Schoenberg B: personal communication, 1981
13. Crapper DR, Quittrat S, Krishnau SS, Dalton AJ, DeBon U: Intranuclear aluminum content in Alzheimer's disease, dialysis encephalopathy and experimental aluminum encephalopathy. Acta Neuropathol (Berl) 50:19–24, 1980
14. Perd DP, Brody AR: Alzheimer's disease: x-ray spectrometric evidence of aluminum accumulation in neurofibrillary tangle-bearing neurones. Science 208:297–299, 1980

15. Terry RD, Davies P: Dementia of the Alzheimer type. Annu Rev Neurosci 3:77–95, 1980
16. Blessed G, Tomlinson BE, Roth M: The association between quantitative measures of dementia and of senile change in the cerebral grey matter of elderly subjects. Br J Psychiatry 114:797–811, 1968
17. Davies P, Maloney AJF: Selective loss of central cholinergic neurons in Alzheimer's disease. Lancet 2:1403, 1976
18. Davies P, Katzman R, Terry RD: Reduced somatostatin-like immunoreactivity in cerebral cortex from cases of Alzheimer's disease and Alzheimer senile dementia. Nature 288:279–280, 1980
19. Johnston MV, McKinney M, Coyle JF: Evidence for a cholinergic projection to neocortex from neurons in basal forebrain. Proc Natl Acad Sci USA 76:5392–5396, 1979
20. Whitehouse PJ, Price DL, Clark AW, Coyle JT, DeLong MR: Alzheimer disease: evidence for selective loss of cholinergic neurons in the nucleus basalis. Ann Neurol 10:122–126, 1981

ADDITIONAL REFERENCES AND PRIOR ART

Bottenstein JE, Sato GH: Growth of a rat neuroblastoma cell line in serum-free supplemented media. Proc Natl Aca Sci USA 76:514–517, 1979

Bradshaw RA: Nerve growth factor. Annu Rev Biochem 47:191–216, 1978

Brown MC, Holland RL, Hopkins WG: Motor nerve sprouting. Annu Rev Neurosci 4:17–42, 1981

Cohen J, Levi-Montalcini R: A nerve growth-stimulating factor isolated from snake venom. Proc Natl Aca Sci USA 42:571–574, 1956

Davies P: Loss of choline acetyltransferase activity in normal aging and in senile dementia. Adv Exp Med Biol 113:251–257, 1978

Finch CE: Catecholamine metabolism in the brains of aging male mice. Brain Res 52:261–276, 1973

Fonnum F: Radiochemical micro assays for the determination of choline acetyltransferase and acetylcholinesterase activities. Biochem J 115:465–472, 1969

Giller EL, Neale JH, Bullock PN, Schrier BK, Nelson PG: Choline acetyltransferase activity of spinal cord cell cultures increased by co-culture with muscle and by muscle-conditioned medium. J Cell Biol 74:16–29, 1977

Hemmendinger LM, Garber BB, Hoffman PC, Heller A: Target neuron-specific process formation by embryonic mesencephalic dopamine neurons in vitro. Proc Natl Acad Sci USA 78:1264–1268, 1981

Hollyday M, Hamburger V: Reduction of the naturally occurring motor neuron loss by enlargement of the periphery. J Comp Neurol 170:311–320, 1976

Hudson AJ: Amyotrophic lateral sclerosis and its association with dementia, parkinsonism and other neurological disorders: a review. Brain 104:217–247, 1980

Johnson DA, Pilar G: The release of acetylcholine from post-ganglionic cell bodies in response to depolarization. J Physiol (Lond) 299:605–619, 1980

Mobley WC, Server AC, Ishii DN, Riopelle RJ, Shooter EM: Nerve growth factor. N Engl J Med 297:1096–1104, 1977

Pestronk A, Drachman DB, Griffin JW: Effects of aging on nerve sprouting and regeneration. Exp Neurol 70:65–82, 1980

Pittman RW, Oppenheim RW: Neuromuscular blockage increases motoneurone arrival during normal cell death in the chick embryo. Nature 271:364–366, 1978

Prochiantz A, DiPorzio U, Kato A, Berger B, Glowinski J: In vitro maturation of mesencephalic dopaminergic neurons from mouse embryos is enhanced in presence of their striatal target cells. Proc Natl Acad Sci USA 76:5387–5391, 1979

Reed DM, Torres JM, Brody JA: Amyotrophic lateral sclerosis and parkinsonian-dementia on Guam, 1945–1972. Am J Epidemiol 101:302–310, 1975

Smith RG, Appel SH: Evidence for a skeletal muscle protein that enhances neuron survival, neurite extension, and acetylcholine (ACh) synthesis. Soc Neurosci Abstr 11:144, 1981

U.S. Pat. No. 4,294,818 discloses a diagnostic method for multiple sclerosis comprised of antibody preparations reactive with antigenic substances associated with lymphocytes.

U.S. Pat. No. 3,864,481 discloses a synthetic amino acid for suppression and diagnosis of multiple sclerosis.

U.S. Pat. Nos. 3,961,894; 4,046,870; and 4,225,576 disclose assay techniques of detecting hormones in the body.

SUMMARY OF THE INVENTION

The present invention is based upon the discovery that ALS, parkinsonism, and Alzheimer disease result from lack of a neurotrophic hormone specific for a particular neuronal network or system which is elaborated or stored in the synaptic target of the affected neurons and exerts a specific effect by acting in a retrograde fashion. Diagnosis and treatment are based on neurotrophic factors which are extracted and tested in three different systems: in ALS the muscle factor which enhances motor neuron survival, growth and development; in parkinsonism the striatal factor which enhances substantia nigra survival, growth and development; and in Alzheimer disease the hippocampus factor which enhances septal neuron survival, growth, and development. These neurotrophic hormones are extracted, purified, and assayed. Diagnosis is accomplished for ALS by assaying motor neurotrophic hormones from muscle in the motor system, for parkinsonism by assaying dopamine neurotrophic hormones from striatum in the nigrostriatal system, and for Alzheimer disease the cholinergic neurotrophic hormone released from the cortex and hippocampus. In case of deficiencies, neurotrophic hormones specific to the particular neuronal network or system are injected in ALS, parkinsonism, and Alzheimer disease.

Accordingly, it is an object of the present invention to provide effective diagnosis and treatment of ALS, parkinsonism, and Alzheimer disease by neurotrophic factors.

It is a further object of the present invention to diagnose ALS by determining or assaying the motor neurotrophic hormone level from muscle in the motor neural system.

It is a further object of the present invention to treat ALS by injecting neurotrophic hormones specific to the motor neural system.

It is a further object of the present invention to diagnose parkinsonism by determining or assaying the dopamine neurotrophic hormone from striatum specific for the nigrostriatal system.

It is a further object of the present invention to treat parkinsonism by injecting neurotrophic hormones specific to the nigrostriatal system.

A further object of the present invention is the diagnosis of Alzheimer disease by determining or assessing the level of cholinergic neurotrophic hormones released from the cortex and hippocampus.

It is a further object of the present invention to provide for the treatment of Alzheimer disease by injecting neurotrophic hormones specific to the septal-hippocampal and nucleus basalis-cortex pathways.

A further object of the present invention is the extraction and purification of neurotrophic hormones specific for the motor system, for the nigrostriatal system, and for cholinergic neurons of the nucleus basalis and septal nucleus.

Other and further objects, features and advantages of the invention are set forth throughout the specification and claims.

DESCRIPTION OF PRESENTLY PREFERRED EMBODIMENTS

From the foregoing, all three diseases can be seen to represent disorders of specific neuronal networks; that is, the motor neuronal system, the nigrostriatal neuronal system and cholinergic neuronal system. All reflect changes in a presynaptic neuronal input with secondary alterations of the target tissue. ALS represents pathological change in Betz cells, cranial motor neurons, and anterior horn cells; parkinsonism, in substantia nigra neurons; and Alzheimer disease, in the cholinergic input from nucleus basalis and septal neurons to cortex and hippocampus, respectively.

The role of neurotrophic hormones of the present invention is a modification of the notion of intrinsic aging of selected neurons; that is, the presence of specific extrinsic factors influence the maintenance and survival of neurons. In each disease, the system degeneration is due to diminished availability of a specific neurotrophic hormone normally released by the postsynaptic cell, taken up by the presynaptic terminal, and exerting its effect by retrograde transport up the presynaptic axon to the soma and nucleus.

Thus, in each of these three neuronal systems, neurotrophic proteins are present in vitro which enhance neuron survival, promote neurite extension, and increase the activity of the neurotransmitter synthetic enzymes in the innervating cell. The same factors responsible for survival of neurons in vitro may also be responsible for their development in vivo. Similar or even the same factors may also be responsible for maintenance of neurons throughout the life cycle in vivo, and may decrease as a normal function of aging.

Thus, a primary manifestation of ALS, Parkinson disease, or Alzheimer disease is failure of the target tissue to supply the necessary neurotrophic hormone. Marked pathological change in the tissue need not be present. Impaired synthesis or release (or both) of the relevant hormone would represent the sine qua non of disease. For example, in the lower motor neuron syndromes of ALS, failure of muscle cells to release the appropriate motor neurotrophic hormone would result in failure of anterior horn cells. The pathological picture would be one of gradual cessation of anterior horn cell function with chromatolysis and of altered nuclear function with minimal evidence of "dying back." Similarly, impairment of Betz cells would result from decreased release of neurotrophic hormone from target neurons. A more precise statement is not possible for the upper motor neuron syndrome since the synaptic target of the descending Betz cell axon is not known with certainty in humans.

In parkinsonism, the neurotrophic failure would be characterized by inability of striatal cells to provide the required dopamine neurotrophic hormone. In Alzheimer disease, the failure would be in hippocampus and cortical cells to supply the relevant cholinergic neurotrophic hormone. Thus, in each system, the lack of an appropriate hormone released from postsynaptic cells impairs the viability of the presynaptic cells. Anterior horn cells, Betz cells, substantia nigra cells, and septal and basal nuclei undergo gradual deterioration.

Thus, motor neurotrophic hormones are released from muscle and are specific for the motor system, dopamine neurotrophic hormones are released from the striatum and are specific for the nigrostriatal system, and cholinergic neurotrophic hormones are released from the cortex and hippocampus and are specific for cholinergic neurons of the nucleus basalis and septal nucleus. With the availability of tissue culture, the presence, deficiency, or absence of specific neurotrophic hormones can be assessed in ALS, parkinsonism, and Alzheimer disease readily and easily.

Motor Neurotrophic Hormone

Skeletal muscle contains protein factors which enhance survival, growth, and cholinergic activity of anterior horn cells in tissue culture.

These neurotrophic hormones, when purified, not only enhance primary growth in tissue culture, but have effects on regeneration in growth of motor nerves in vivo. The potential benefits of such substances are unlimited for patients with nerve injuries due to trauma, infection, or other causes. One of the significant degenerative conditions of mankind, namely amyotrophic lateral sclerosis, represents a deficiency in such a neurotrophic hormone. Extraction of skeletal muscle provides a readily available, relatively specific source for motor neurotrophic factors and provides sufficient quantities for purification and characterization.

Extraction and Partial Purification

Skeletal muscle from newborn rats or 5–6 month fetal calves is homogenized in three volumes of phosphate buffered saline at pH 7.4 at 4° and centrifuged at 32,000 g for one hour. The resulting supernatant is recentrifuged at 100,000 g for two hours, and dialyzed for 14 hours against phosphate buffered saline. The neurotrophic substance is stable to freezing at minus 70° and to lyophilization. It is labile to heating such that one-half the activity is lost after 25 minutes at 60 degrees. It is also labile to tryptic or protease digestion. It is precipitated in 35–60% ammonium sulfate with retention of activity. Sephadex gel filtration chromatography indicates a molecular weight of greater than 40,000. The purified preparations are greater than 100 fold pure; however, further purification is desirable.

Assay of Neurotrophic Hormone

Spinal cord cultures are obtained from arachnoid-free ventral cord of stage 24–27 rat embryos. After dissociation, cells are plated at $2 \times 10^6$ cells/dish onto polylysine coated culture dishes. Cytosine arabinoside ($1 \times 10^{-5}$) is added to the growth medium one day after cell plating, and is maintainted in that medium until the muscle extract was added. In addition, other cultures are maintained without cytosine arabinoside. Within three days of application of the muscle extract (50 to 450 mg/ml), there is a clustering of neuronal and glial cells. At four days there is a 1.5 fold increase in cell survival, a 4 fold increase in the average number of neurites per neuron, and a 3.5 fold increase in the average neuritic length. There is a 3 fold increase in acetylcholine synthesis, and a 3 fold increase in choline acetyl transferase approximately four days after the addition of muscle extract to ventral cord cells.

Treatment

If there is a deficiency of motor neurotrophic hormone, treatment is accomplished by injecting these hormones.

Dopaminergic Neurotrophic Hormone

Extracts of the corpus striatum of the mammalian brain influence the survival, development and differentiation of substantia nigra tissue. The importance of this isolation and purification is that such a factor may not only play a role in the development of dopaminergic innervation during development, but it may also play a role in maintenance of such innervation. Thus, in diseases such as Parkinson's disorder in which substantia nigra cells are lost, such a dopaminergic neurotrophic factor may be deficient. Replacement of this particular neurotrophic hormone may have salutary effects on the clinical syndrome of Parkinson's disease.

Extraction and Purification

Striatum tissue from various aged rat brains are frozen and thawed one time, and then sonicated for 30 seconds in three volumes of phosphate-buffered saline. The resulting extract is spun at 4° for 90 minutes at 100,000 g, and is used as such. At the present time no further purification of this extract has been undertaken, but the protein nature of the extract has been determined. Treatment of the striatal extract with 0.1% (weight/volume) trypsin at 25° for 90 minutes abolishes 93% of the activity. Heat also inactivates the neurotrophic factor. All activity is lost at 95° for 30 minutes, 50% of activity is lost at 60° for five minutes.

Assay for Neurotrophic Activity

Substantia nigra tissue from 15-day embryonic rat midbrain is dissected into 0.3 mm diameter, and 20–30 pieces of specimens are explanted onto poly-L-lysine-coated 35 mm plastic culture dishes. The culture is maintained in 2 ml of modified Sato's media (3 mM glutamine, 50 mg/ml glucose, 25 mg garamycin, 3.0 mg insulin, 50 mg transferin, 20 nM progesterone, 100 mM putrescine, 30 mM selenium and 500 ml of Dulbecco's Minimal Eagle's Media. All cultures are incubated in 10% $CO_2$ at 36°. Extracts of striatum are added on day 2 to 3 and monitored for the following week. Morphologic changes are noted within the first two days as an increase in process length and process density. In addition, specific dopamine uptake is measured. Blockade by the antagonist, benztropine, specifically defines the dopamine uptake as belonging to neurones of the nigrostriatal pathway. The ability of striatal extract to enhance process growth, and specific dopamine uptake were not noted with extracts from occipital cortex, spinal cord, liver, and muscle. The activity of the striatal extract on dopamine uptake is age dependent. Striatal tissue from 10 day old rats has maximal activity, and striatal tissue from adult rats has 50% of the activity of 10 day old rats.

Treatment

If there is a deficiency in dopaminergic neurotrophic hormone, treatment is accomplished by injecting these hormones.

Hippocampal Cholinergic Neurotrophic Hormone

Extracts of hippocampal tissue appear to exert a survival, differentiating, development, and possibly maintenance effect on medial septal neurones in culture. This system is analogous to the previous two, in that target-derived diffusible neurotrophic factors play an important role in the survival and differentiation of innervating neurones in tissue culture. The applicability of this system is primarily in those conditions where there is a loss of medial septal neurones, and neurotrophic hormones derived from the hippocampus may play a role, either in enhancing regeneration of neurites, or even promoting development of septal tissue transplanted into mammalian brains. The most significant clinical syndrome to which this may be applied is that of Alzheimer's disease, or senile dementia. In this condition, there is a dramatic loss of the neurones of medial septal region as well as nucleus basalis of Meynert. Thus, the availability of the hippocampal neurotrophic hormone allows one to assay for the amount of such a hormone present in Alzheimer's disease, and if it is deficient, to replace it. Such a neurotrophic hormone may also foster the improvement of memory function in patients with traumatic, neoplastic, as well as vascular, lesions of the brain. It may also be useful in enhancing transplants of cholinergic brain tissue. Soluble extracts of hippocampus enhance neuritic outgrowth and cholinergic activity of medial septal nucleus cultured in serum free, defined media. The enhancement of both neuritic outgrowth and cholinergic activity is dose dependent specific for hippocampal extract and varies with age, reaching a peak in two to three week old hippocampus. The enhancing activity is mediated by protein since it is heat labile and inactivated by proteases.

Preparation of Hippocampal Tissue Extract

Hippocampal tissue from rat brain of different ages is frozen and thawed one time, and then sonicated for 30 seconds in three volumes of phosphate-buffered saline. The supernatant is collected after spinning down at 4° for 90 minutes. Subsequent experiments have indicated that spinning for six hours at 100,000 g at 4° provides a five fold purification of the supernatant activity. At the present time no further purification has been undertaken. The supernatant activity is heat labile with 50% of the activity lost after eight minutes at 60°. Activity is completely lost at 95° for 30 minutes. Trypsin and protease inactivate both morphologic and cholinergic activity of the neurotrophic factor.

Prolonged centrifugation for six hours yields two fractions: a supernatant fraction which is heat labile and a separate pellet activity which is heat stable. The two activities are distinct, since even after fully saturating with the pellet activity, the addition of supernatant gives two fold enhancement of cholinergic activity.

Hippocampal tissue is dissected in ice-cold PBS pH 7.2. 0.65 g (wet weight) hippocampal tissue can be obtained from ten 2-week old rats. Tissue is frozen and thawed and then sonicated for 30 seconds at grade 35 with a Sonic 300 Dismembrator (Artek System Corporation) in two volumes of PBS, and the supernatant collected after centrifugation at 4° for 90 minutes at 100,000 g. Protein concentration was usually 7-8 mg/ml.

Medial Septal Tissue Culture Assay

Medial septal nucleus tissue from 16-day embryonic rat brain is dissected into 0.3 mm diameter pieces, and 20-30 such specimens are explanted onto poly-L-lysine-coated plastic tissue culture dishes. The culture is maintained in 2 ml of serum-free, chick embryonic extract-free, modified Sato's media as indicated in the tissue culture conditions for substantia nigra. The cells become attached to the culture dish surface within one hour and being to extend processes within 24 hours after explanation. The addition of hippocampal extract at day 3 results in enhancement of fiber length as well as fiber outgrowth density. In addition, there is a five fold increase in acetylcholine synthesis after six days in vitro. The effect is specific for hippocampal tissue, since extract from cerebral cortex, striatum, cerebellum, spinal cord, muscle, kidney, and liver produce only minimal effects. Also, age is an important variable with two- to three-week hippocampal extract being the most potent and adult tissue having less than half the activity.

Treatment

If there is a deficiency in a hippocampal neurotrophic hormone, treatment is accomplished by injection of the hormone. (Injection may have to be intraventricularly).

Techniques By Which Extracts Are Purified

1. Ion Exchange Chromatography

Muscle neurotrophic factor is purified on DEAE ion exchange columns eluting at 0.15-0.35 M NaCl at pH 7.4.

2. Molecular Weight Filtration

Hippocampal extract is purified by passing through a YM5 filter which retards molecules greater than 5000 daltons and the substance which is smaller than 5000 daltons is then purified on a P2 column. The active factor has been found to be between 5000 and 2000 daltons in molecular weight by this procedure.

3. Electrophoretic Separation

Isoelectric focusing techniques have established the $P_I$ of the muscle extract activity as 5.0.

4. Polyclonal and Monoclonal Antibodies

These immunologic techniques enable the raising of specific markers for the neurotrophic factors of use in further purification by affinity-chromatography, and for use in diagnosis by radioimmunoassay.

While the foregoing examples have used animal tissue, it is the practice in the art to use animal tissue from which it is predictable that human tissue will give substantially the same results.

The present invention, therefore, is well suited and adapted to attain the objects and ends and has the advantages and features mentioned as well as others inherent therein.

While presently preferred embodiments of the invention have been given for the purpose of disclosure, changes can be made therein which are within the spirit of the invention as defined by the scope of the appended claims.

What is claimed is:

1. A method to diagnose the presence of ALS in a subject by detecting a deficiency of specific neurotrophic activity in said subject as compared to normal controls, wherein said deficiency is detected by the method which comprises
    extracting the proteins from skeletal muscle tissue of said subject;
    assaying said extract for neurotrophic activity with respect to the neuronal system normally associated with said skeletal muscle tissue; and
    comparing said neurotrophic activity to activity exhibited in the same assay by similar extracts from skeletal muscle tissue of controls.

2. The method of claim 1 wherein said extract is prepared by homogenizing skeletal muscle in buffer and recovering the extract.

3. The method of claim 1 wherein said neurotrophic activity assay comprises treating embryonic ventral cord cells with said extract.

* * * * *